US00PP24315P2

(12) United States Plant Patent
Williams

(10) Patent No.: US PP24,315 P2
(45) Date of Patent: Mar. 18, 2014

(54) ***MUSA* PLANT NAMED 'MEKONG GIANT'**

(50) Latin Name: ***Musa intinerans* var. *xishuangbannaens***
Varietal Denomination: MeKong Giant

(75) Inventor: Brian Paul Williams, Louisville, KY (US)

(73) Assignee: Brian's Botanicals, Louisville, KY (US)

( * ) Notice: Subject to any disclaimer, the term of this patent is extended or adjusted under 35 U.S.C. 154(b) by 52 days.

(21) Appl. No.: 13/507,213

(22) Filed: Jun. 13, 2012

(51) Int. Cl.
*A01H 5/00* (2006.01)

(52) U.S. Cl.
USPC ..... Plt./160

(58) Field of Classification Search
USPC ..... Plt./160
See application file for complete search history.

*Primary Examiner* — Kent L Bell
(74) *Attorney, Agent, or Firm* — Penny J. Aguirre

(57) ABSTRACT

A new cultivar of *Musa* plant named 'MeKong Giant', that is characterized by its large green leaves with red coloration on the lower surface of the young leaves, its very fast growth habit and large stature, its good cold hardiness, its thick trunks that are streaked with dark pink to dark maroon with age, and its large underground rhizomes with new growth that returns quickly from winter dormancy.

3 Drawing Sheets

Botanical classification: *Musa intinerans* var. *xishuangbannaens*.

Cultivar designation: 'MeKong Giant'.

BACKGROUND OF THE INVENTION

The present invention relates to a new and distinct cultivar of *Musa intinerans* var. *xishuangbannaens* known as 'MeKong Giant', and is hereinafter referred to as 'MeKong Giant'. 'MeKong Giant' is a new cultivar of hardy banana grown for landscape use.

The Inventor selected the new cultivar, 'MeKong Giant', as a single unique plant in a seedbed at his nursery in Louisville, Ky. in 1993. The seedbed had been planted with 500 seeds collected from an unnamed plant of *Musa intinerans* var. *xishuangbannaens*. The male parent is unknown.

Asexual reproduction of the new cultivar was first accomplished utilizing root cuttings by the Inventor in Eustis, Fla. in 2003. Asexual reproduction by root cuttings and in vitro propagation of the new cultivar has shown that the unique features of 'MeKong Giant' are stable and reproduced true to type in successive generations.

SUMMARY OF THE INVENTION

The following traits have been repeatedly observed and represent the characteristics of the new cultivar. These attributes in combination distinguish 'MeKong Giant' as a new and unique cultivar of *Musa*.

1. 'MeKong Giant' exhibits large green leaves with red coloration on the lower surface of the young leaves.
2. 'MeKong Giant' is very fast growing and of large stature; reaches 3.6 to 9 m in height and about 3.6 to 6 m in spread depending on growing conditions.
3. 'MeKong Giant' is very cold hardy and is hardy in U.S.D.A. Zones 6 to 11.
4. 'MeKong Giant' exhibits thick trunks that are streaked with dark pink to dark maroon with age.

5. 'MeKong Giant' exhibits large underground rhizomes with new growth returning quickly from winter dormancy.

'MeKong Giant' can be distinguished from its female parent, which differs from 'MeKong Giant' in having trunks that are light green in color and in having leaves that lack the red coloration on the lower surface of the leaves. 'MeKong Giant' can be most closely compared to plants of the species *Musa basjoo* that is similar in cold hardiness and *Musa* 'Saba' (not patented) that is similar in producing large trunks. Plants of *Musa basjoo* differs from 'MeKong Giant' in having green trunks, in lacking red coloration on the lower surface of the leaves, and in returning from dormancy less quickly. *Musa* 'Saba' differs from 'MeKong Giant' in being not as cold hardy and in producing green trunks.

BRIEF DESCRIPTION OF THE DRAWING

The accompanying colored photographs illustrate the overall appearance and distinct characteristics of the new *Musa*. The photographs were taken of shoots emerged from 7 year-old rhizomes as grown outdoors in a trial garden in Louisville, Ky.

Figure 1:
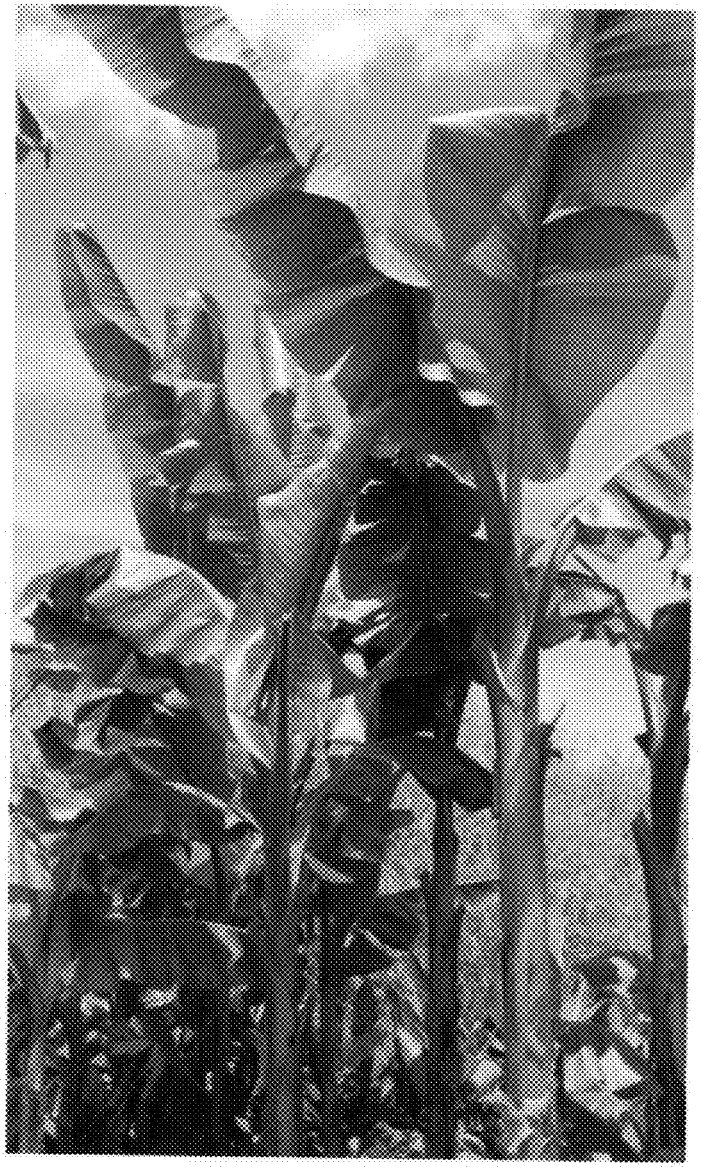
FIG. 1 provides a side view of plants of 'MeKong Giant' in summer.
Figure 2:
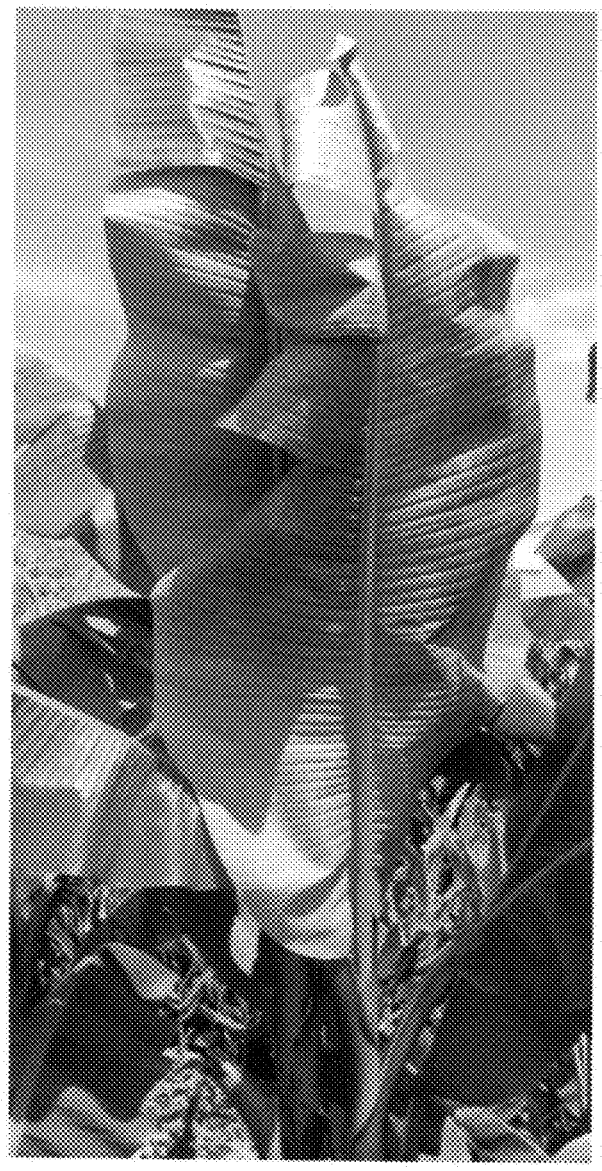

The photograph in FIG. 2 provides a view of the lower leaf surface of new leaves of 'MeKong Giant'.

Figure 3:
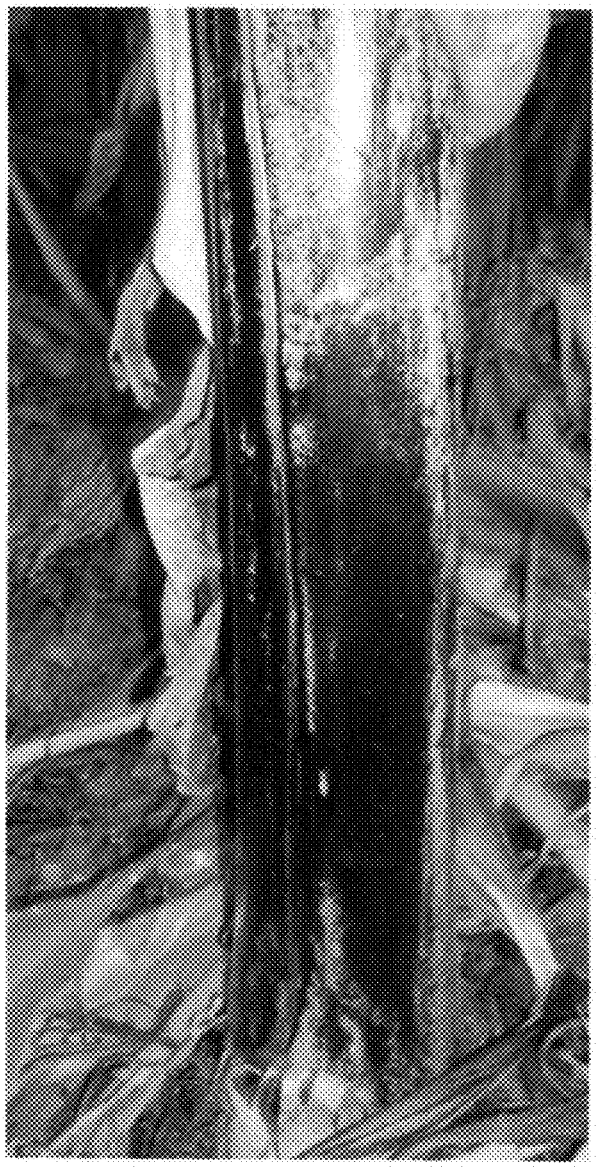

The photograph in FIG. 3 provides a view of the trunk coloration of 'MeKong Giant'.

The colors in the photographs are as close as possible with the photographic and printing technology utilized and the color values cited in the Detailed Botanical Description accurately describe the colors of the new *Musa*.

DETAILED BOTANICAL DESCRIPTION OF THE PLANT

The following is a detailed description of shoots emerged from 7 year-old rhizomes as grown outdoors in a trial garden in Louisville, Ky. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Mid to late summer in Louisville, Ky.

*Plant type.*—Deciduous, tropical, perennial, arise annually from rhizomes, new growth arises quickly from winter dormancy.

*Plant habit.*—Upright, tufted leaves producing thick stems from petioles (pseudostems).

*Height and spread.*—Reaches 3.6 to 9 m in height and about 3.6 to 6 m in spread depending on growing conditions.

*Hardiness.*—U.S.D.A. Zones 6 to 11.

*Diseases and pests.*—No diseases and pests problems have been observed.

*Roots.*—Fleshy, emerge from corms and rhizomes.

*Corms.*—An average of 14 cm in width and 10 cm in depth, scaly and fibrous surface, primarily a blend of 199C and 200B in color.

*Rhizomes.*—Can grow up to 1.5 m in length and 13 cm in width, 199C in color with areas of 200A.

*Propagation type.*—In vitro propagation is preferred.

*Growth rate.*—Very vigorous.

Trunk description (pseudostem):

*Trunk size.*—An average of 80 cm in length and 2 cm in width (with sheaths).

*Trunk type.*—Sturdy, surrounded by sheathed leaf petioles.

*Trunk color.*—151A, suffused with 166B becoming heavily suffused with 183A and 200A with age, especially near base.

*Petioles.*—Newly emerging; a color between N144A and 145A and sulcate, sheathing to base to comprise trunk, free portion; about 15 cm in length 2 cm in length, sheathed portion; length of trunk in length and about 6 cm in width, defined by trunk color.

*Petiole surface.*—Glabrous and shiny, older free petioles become papery with leaf blade drop and N199 in color with streaks of 203A.

Foliage description:

*New shoots.*—An average of 20 cm in length and 1 cm in width prior leaf unfurling, 145B in color.

*Leaf shape.*—Elliptic-lanceolate.

*Leaf division.*—Simple.

*Leaf base.*—Cuneate-rounded.

*Leaf apex.*—Acute.

*Leaf venation.*—Pinnate, mid rib is sulcate, upper surface; a color between 138B and 138C, lower surface; mid rib is conspicuous and protruding, 183B and 183C in color and blending with N144A near base.

*Leaf margins.*—Entire, slightly undulating.

*Leaf attachment.*—Petiolate.

*Leaf arrangement.*—Alternate with petioles sheathed.

*Leaf surface.*—Glabrous and satiny on upper surface and glabrous and a sheen on lower surface.

*Leaf orientation.*—Emerge upright and become outward at about a 45° angle when mature.

*Leaf color.*—Newly emerged foliage; 138B on upper and lower surface, maturing foliage upper surface; N138B, maturing foliage lower surface; a blend of 146C and 146D and suffused with 178B, mature foliage upper surface; N138B, mature foliage lower surface; a blend of 146C and 146D.

*Leaf size.*—Average of 65 cm in length and 30 cm in width.

Inflorescence description: The original plant of 'MeKong Giant' has been observed by the inventor for 15 years and flowers have not been observed.

Fruit and seed: The original plant of 'MeKong Giant' has been observed by the inventor for 15 years and fruit have not been observed.

It is claimed:

1. A new and distinct cultivar of *Musa* plant named 'MeKong Giant' as herein illustrated and described.

* * * * *